United States Patent
Pacheco

(10) Patent No.: US 7,491,180 B2
(45) Date of Patent: Feb. 17, 2009

(54) APPARATUS AND METHODS FOR TEMPLATING AND PLACEMENT OF ARTIFICIAL DISCS

(76) Inventor: Hector O. Pacheco, 4701 Rosinante Rd., El Paso, TX (US) 79922

( * ) Notice: Subject to any disclaimer, the term of this patent is extended or adjusted under 35 U.S.C. 154(b) by 0 days.

(21) Appl. No.: 11/819,497

(22) Filed: Jun. 27, 2007

(65) Prior Publication Data

US 2008/0009945 A1 Jan. 10, 2008

Related U.S. Application Data

(60) Provisional application No. 60/816,882, filed on Jun. 28, 2006.

(51) Int. Cl.
| | |
|---|---|
| A61B 5/103 | (2006.01) |
| A61B 5/117 | (2006.01) |
| A61B 19/00 | (2006.01) |
| A61B 5/00 | (2006.01) |
| A61B 18/18 | (2006.01) |
| A61B 17/56 | (2006.01) |
| A61B 17/58 | (2006.01) |
| A61B 17/70 | (2006.01) |
| A61B 17/60 | (2006.01) |
| G01M 19/00 | (2006.01) |
| A61F 5/04 | (2006.01) |
| A61F 2/30 | (2006.01) |
| A61F 5/00 | (2006.01) |
| A61F 2/00 | (2006.01) |
| A61F 2/02 | (2006.01) |
| A61F 2/28 | (2006.01) |
| A61F 2/44 | (2006.01) |

(52) U.S. Cl. .................. 600/594; 600/587; 600/595; 128/898; 128/920; 128/922; 128/923; 73/172; 606/50; 606/53; 606/60; 606/246; 606/248; 606/249; 606/86 R; 606/96; 606/97; 606/98; 606/99; 606/102; 623/11.11; 623/16.11; 623/17.11; 623/17.17; 623/902; 623/908

(58) Field of Classification Search .................. 600/587, 600/594; 128/898, 920, 922, 923; 73/172; 606/50, 53, 61, 246, 248, 249, 86 R, 96, 97, 606/98, 99, 102; 623/11.11, 16.11, 17.11, 623/17.17, 902, 908
See application file for complete search history.

(56) References Cited

U.S. PATENT DOCUMENTS

| | | |
|---|---|---|
| 5,291,537 A | 3/1994 | Mazess |
| 5,351,404 A | 10/1994 | Smith |
| 5,682,886 A | 11/1997 | Delp |
| 5,748,767 A | 5/1998 | Raab |
| 5,772,594 A | 6/1998 | Barrick |

(Continued)

Primary Examiner—Max Hindenburg
Assistant Examiner—Jeffrey G Hoekstra
(74) Attorney, Agent, or Firm—Nixon & Vanderhye

(57) ABSTRACT

A method of determining the size and/or placement of a prosthetic disc in a disc space between adjacent endplates of two vertebrae in a selected spinal area, comprising: using a computer to identify the disc space parameters of height, width, depth and lordosis between the adjacent vertebral endplates; using a computer to create an artificial volume corresponding to an actual prosthetic disc that can be positioned in the disc space in accordance with a manufacturer's size and lordosis specifications for prosthesis; using a computer to determine the center of the disc space and the center of rotation of the prosthetic disc volume; using a computer to position the prosthetic disc volume in the disc space such that the center of rotation of the prosthetic disc volume is positioned posterior to the center of the disc space; and using a computer to determine the prosthetic disc volume that fits within the disc space in accordance with a surgeon's or manufacturer's specification for prosthesis.

17 Claims, 15 Drawing Sheets

U.S. PATENT DOCUMENTS

| | | |
|---|---|---|
| 5,799,055 A | 8/1998 | Peshkin |
| 5,850,836 A | 12/1998 | Steiger |
| 5,871,018 A | 2/1999 | Delp |
| 6,002,959 A | 12/1999 | Steiger |
| 6,069,932 A | 5/2000 | Peshkin |
| 6,167,296 A | 12/2000 | Shahidi |
| 6,175,758 B1 | 1/2001 | Kambin |
| 6,198,794 B1 | 3/2001 | Peshkin |
| 6,226,548 B1 | 5/2001 | Foley |
| 6,282,437 B1 | 8/2001 | Franck et al. |
| 6,351,662 B1 | 2/2002 | Franck et al. |
| 6,470,207 B1 | 10/2002 | Simon et al. |
| 6,477,400 B1 | 11/2002 | Barrick |
| 6,484,044 B1 | 11/2002 | Lilienfeld-Toal |
| 6,490,467 B1 | 12/2002 | Bucholz et al. |
| 6,490,475 B1 | 12/2002 | Seeley et al. |
| 6,529,765 B1 | 3/2003 | Franck et al. |
| 6,546,277 B1 | 4/2003 | Franck et al. |
| 6,697,664 B2 | 2/2004 | Kienzle, III et al. |
| 6,741,883 B2 | 5/2004 | Gildenberg |
| 7,235,076 B2 | 6/2007 | Pacheco |
| 2002/0161368 A1 | 10/2002 | Foley et al. |
| 2004/0092932 A1 | 5/2004 | Aubin et al. |

| DISC SPACE | CORONAL | SAGITTAL | TRANSAXIAL |
|---|---|---|---|
| L4/5 | | | |

| Intervertebral Disc Space | Height (mm) | Width (mm) | Depth (mm) | Lordosis (mm) |
|---|---|---|---|---|
| Lumber L1/L2 | 10 | 40 | 20 | 0 |
| Lumber L2/L3 | 11 | 45 | 25 | 0 |
| Lumber L3/L4 | 10 | 45 | 25 | 5 |
| Lumber L4/5 | 12 | 45 | 25 | 5 |
| Lumber L5/S1 | 12 | 48 | 30 | 10 |
| Etc. | | | | |

APPARATUS AND METHODS FOR TEMPLATING AND PLACEMENT OF ARTIFICIAL DISCS

CROSS REFERENCE TO RELATED APPLICATION

This application claims the benefit of U.S. Provisional Patent Application No. 60/816,882 filed on Jun. 28, 2006.

BACKGROUND OF THE INVENTION

1. Field of the Invention

The present invention relates to the templating and placement of prosthetic intervertebral discs and, more particularly, to new and improved apparatus and methods for enabling a physician to select the optimal size of a prosthetic disc and to position it accurately between vertebrae to optimize its dynamic function.

2. Description of the Background Art

The degeneration of human intervertebral discs is increasingly being treated with prosthetic intervertebral discs. The critical parameters for a successful surgical outcome are appropriate templating and placement of the prosthetic disc during artificial disc replacement spine surgery. For templating, the critical parameters are height, width, depth and lordosis. For placement, there are different approaches of placing these artificial discs. Specifically, they can be placed anteriorly, laterally or posteriorly. The most common of these approaches is the anterior approach. A critical component of positioning of the prosthetic disc is the anterior-posterior position as this determines the center of rotation through the prosthesis and hence its dynamic function. If the prosthesis is placed anterior to the center of the disc space then the prosthesis will essentially function as a rigid device. Ideal placement of the prosthesis requires its instantaneous center of rotation to be in the posterior one-third of the disc space posterior to the center of the actual disc space. Templating of appropriate artificial disc implant size selection is often finalized at time of surgery. Subsequent placement of the prosthetic disc is aided by fluoroscopic or other image guidance.

To date many of the proprietary templating and placement systems and methods are manually determined by the surgeon at the time of surgery. As of yet, no apparatus or system is available which will automatically determine the ideal height, width, depth and lordosis or actual placement of an artificial intervertebral disc prosthesis.

BRIEF SUMMARY OF THE INVENTION

The present invention will automatically generate a table providing the height, width, depth and lordosis of both the actual disc space and an individual prosthetic or artificial disc, and will also generate a schematic diagram illustrating this data for individual intervertebral disc spaces, This method in effect establishes two dimensionally true different volumes. Specifically, it creates the actual volume of the disc space and then also incorporates the volume created by the prosthetic disc. The volumes are displayed individually and merged together to allow the surgeon to determine ideal prosthetic disc selection. A key feature of the merged volume image is center of rotation coordinates within these volumes to assure ideal prosthetic implant size and position to optimize dynamic function through the prosthetic disc range of motion. This data can then be utilized by the surgeon for actual prosthetic disc replacement by one of four methods: 1. Method A: manual artificial disc placement by the surgeon's preferred method; 2. Method B: utilize pedicle base circumference outline method combined with intraoperative fluoroscopy; 3. Method C: automated prosthetic disc placement using a two ring aligning apparatus and drill guide method; and 4. Method D: with any commercially available registration software (e.g., computed tomography/fluoroscopy, etc). These methods are embodied in the present invention.

DESCRIPTION OF THE PREFERRED EMBODIMENTS

The methods and apparatus of templating and placement of prosthetic intervertebral discs in accordance with the present invention are set forth in more detail hereinafter.

Step 1

A computed tomography scan (CT), magnetic resonance image (MRI), CT capable fluoroscopy or similar two-dimensional imaging study of the spine area of interest may first be obtained. Thin cut sections are preferable to increase accuracy and detail.

Step 2

Figure 1A:
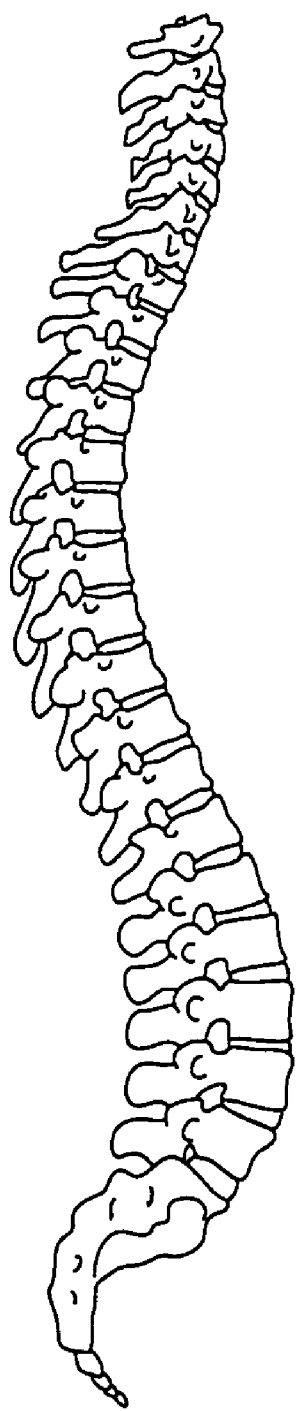
FIGS. 1a and 1b are three dimensional computer images of the side and back, respectively, of the bony spine made from CT, MRI or other studies of the spine area of interest.
Figure 1B:
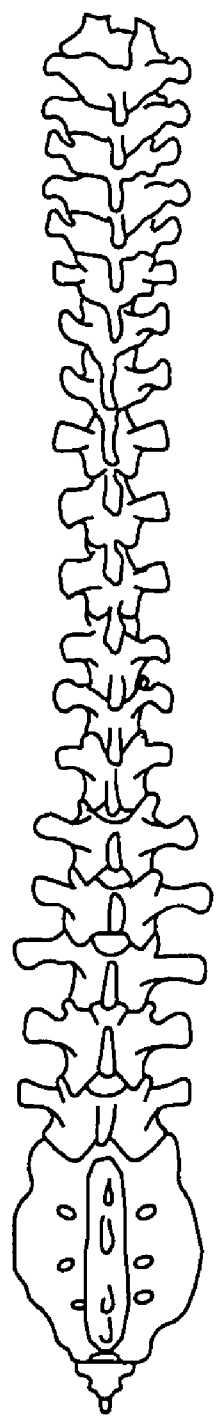
Figure 2:
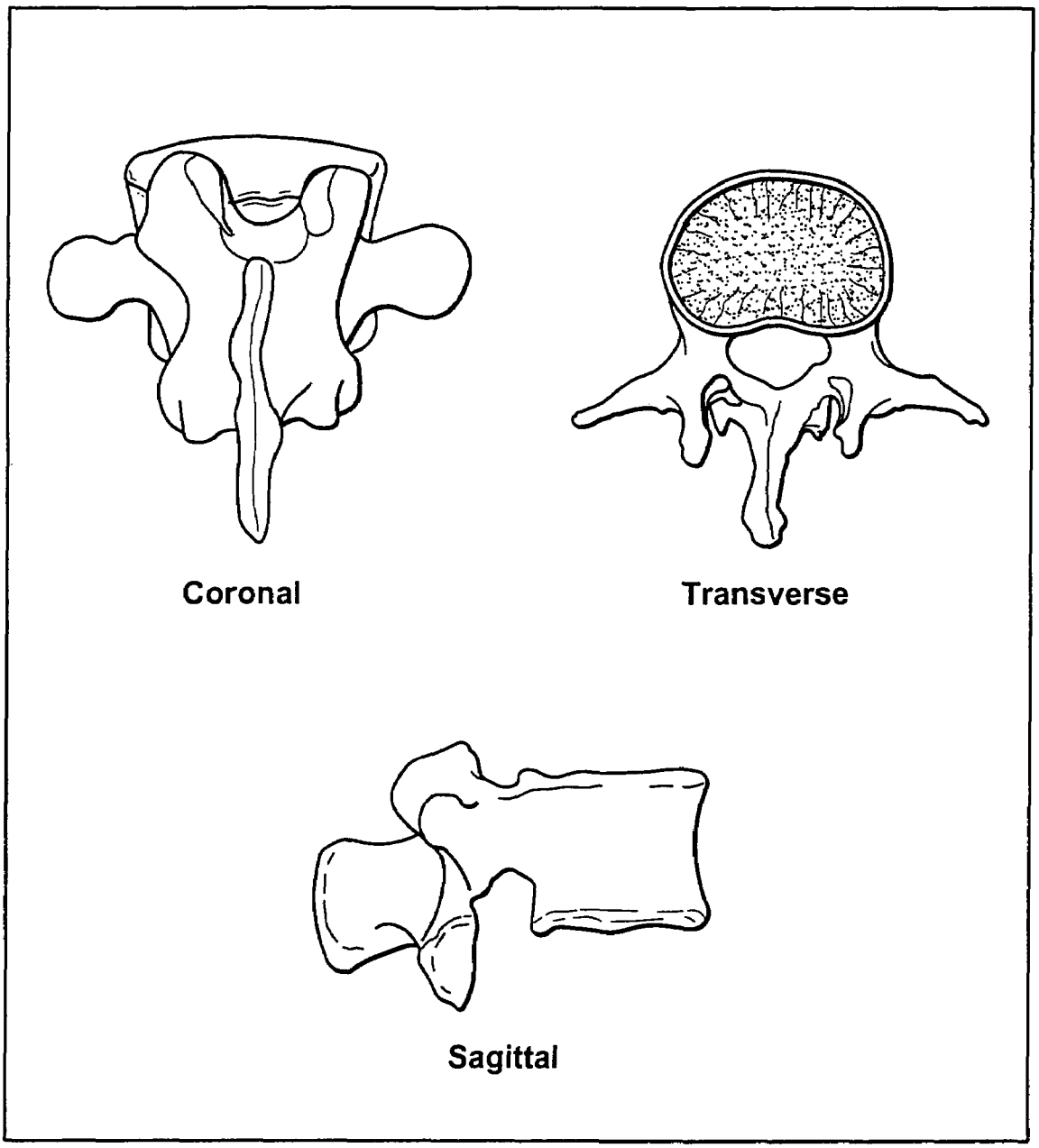
FIG. 2 illustrates three dimensional computer images of individual vertebra undergoing a manual eggshell corpectomy from the spine area shown in FIG. 1a and FIG. 1b.
Figure 3:
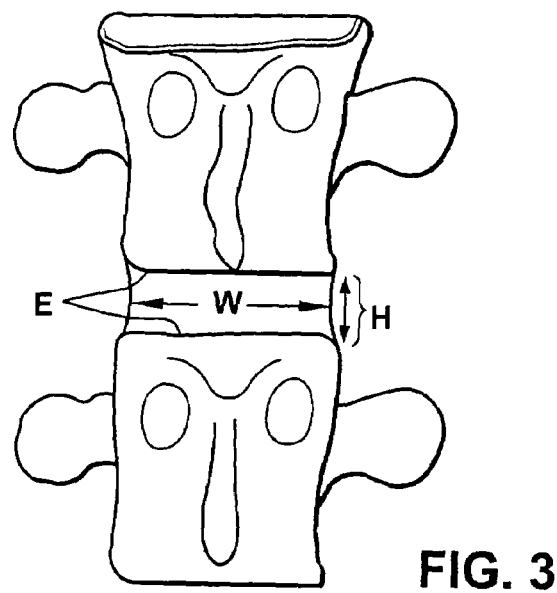
FIG. 3 is a schematic coronal elevational view of two adjacent vertebrae and the disc space therebetween.
Figure 4:
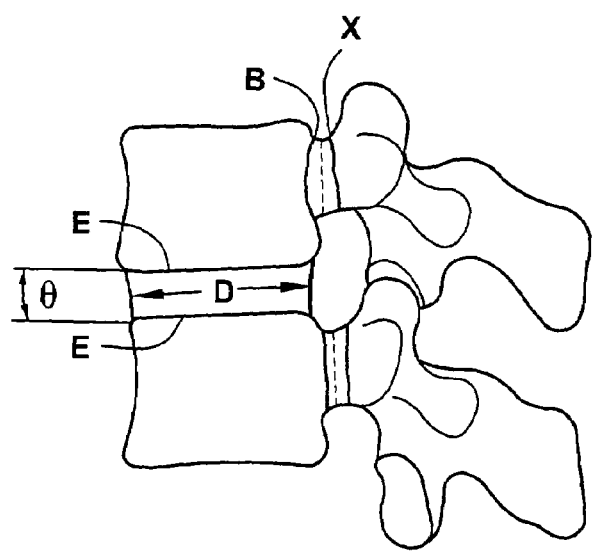
FIG. 4 is a schematic sagittal elevational view of the vertebrae shown in FIG. 3.
Figure 5:
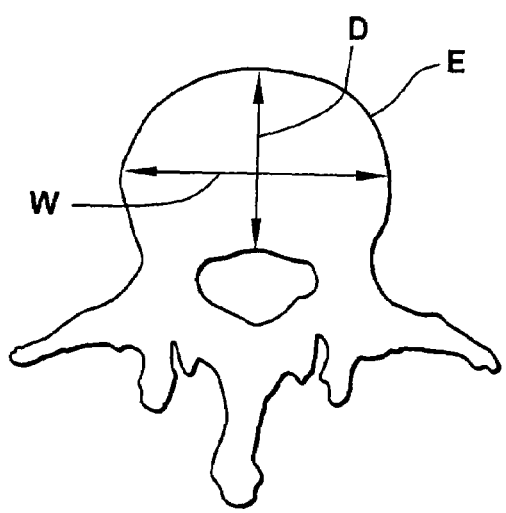
FIG. 5 is a schematic transverse plan view of the upper vertebra shown in FIGS. 3 and 4.
Figure 6:
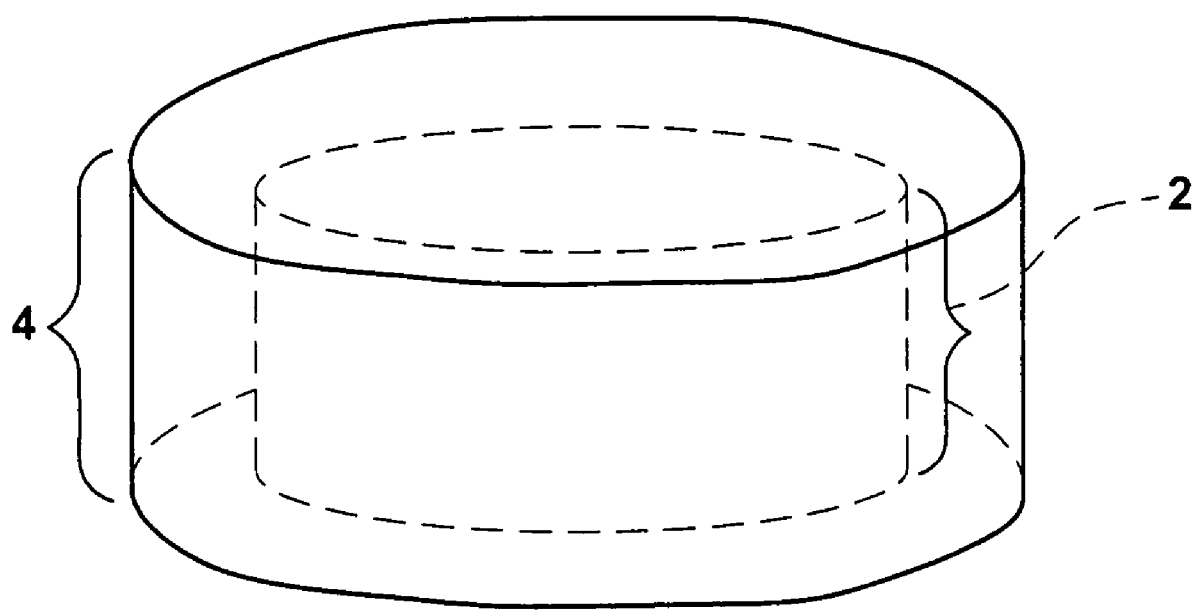
FIG. 6 is a schematic perspective view of a prosthetic disc positioned within the disc volume between the adjacent vertebrae shown in FIGS. 3, 4 and 5.
Figure 7:
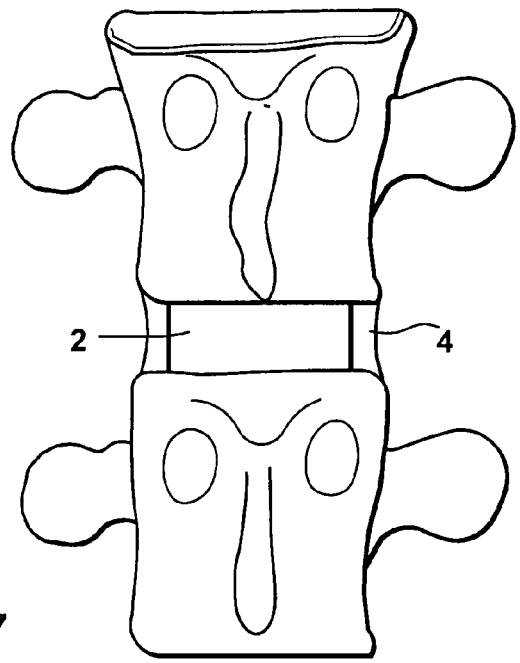
FIG. 7 is a schematic coronal elevational view of the vertebrae shown in FIGS. 3-5 with the prosthetic disc of FIG. 6 positioned therebetween.
Figure 8:
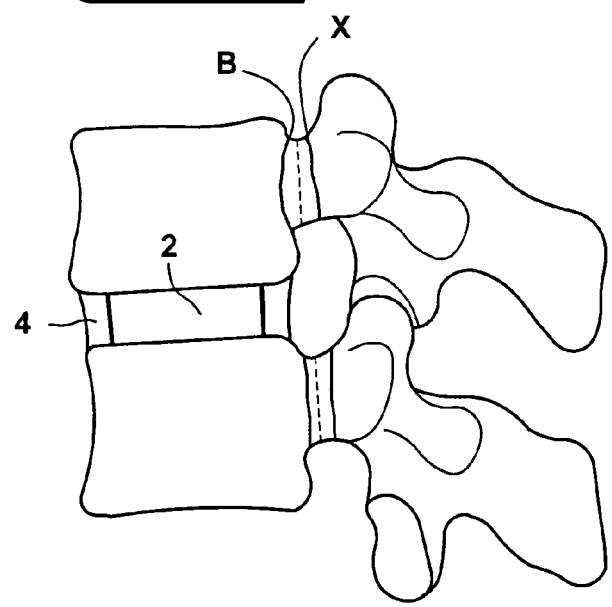
FIG. 8 is a schematic sagittal elevational view of the vertebrae and prosthetic disc shown in FIG. 7.
Figure 9:
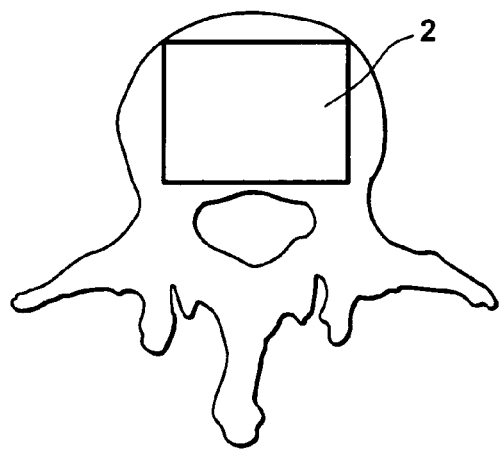
FIG. 9 is a schematic transverse plan view of the vertebrae and prosthetic disc shown in FIGS. 7 and 8.

A dimensionally true three dimensional computer image of the bony spine is made from the CT, MRI or other studies or in any other suitable manner, as shown in FIGS. 1a and 1b.

Step 3

The three dimensional individual vertebra as shown in FIGS. 2-5 are utilized to determine the intervertebral disc space volume parameters of height H, width W, depth D and lordosis θ between adjacent vertebral endplates E. B represents the pedicle base circumference and X represents the pedicle isthmus in FIG. 4.

Step 4

Figure 10:
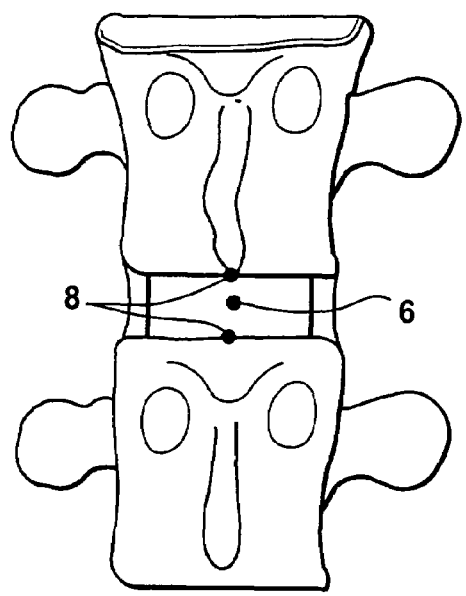
FIG. 10 is a coronal view similar to FIG. 7 showing the center of rotation of the prosthetic disc and the center of the disc space between the vertebrae.
Figure 11:
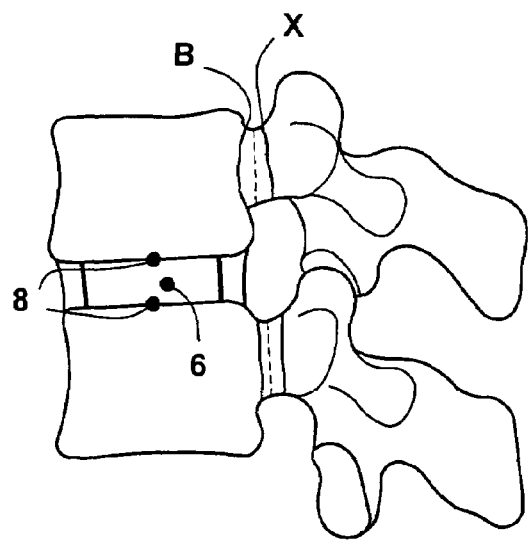
FIG. 11 is a sagittal view similar to FIG. 8 showing the center of the rotation of the prosthetic disc and the center of the disc space between the vertebrae.
Figure 12:
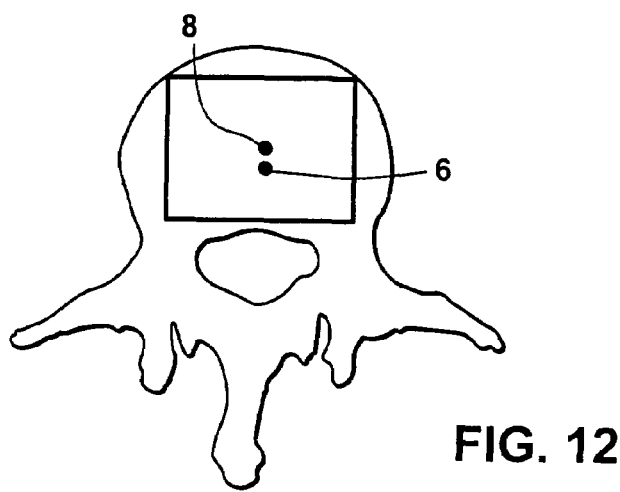
FIG. 12 is a transverse view similar to FIG. 9 showing the center of rotation of the prosthetic disc and the center of the disc space between the vertebrae.
Figure 13:
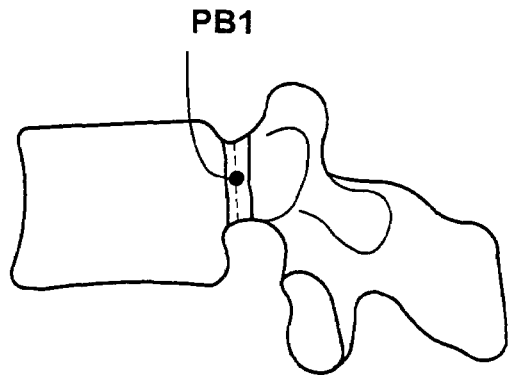
FIG. 13 is a schematic sagittal view of a vertebra showing the medial center of the pedicle base circumference.
Figure 14:
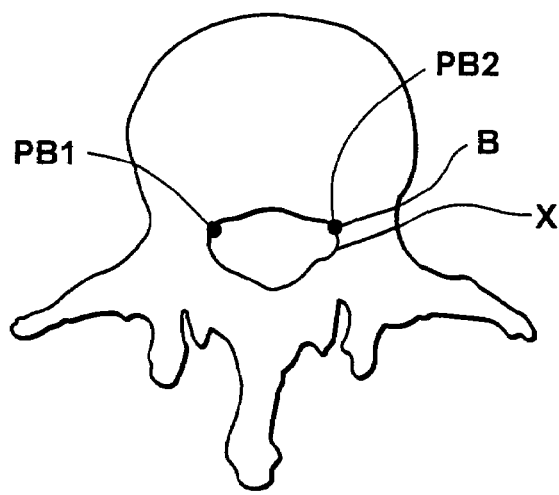
FIG. 14 is a schematic transverse view of the vertebra shown in FIG. 13 showing the medial centers of the pedicle base circumferences and the isthmus of a pedicle.
Figure 15:
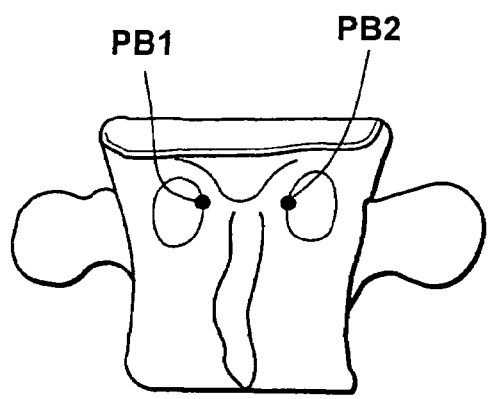
FIG. 15 is a schematic coronal view of the vertebra shown in FIGS. 13 and 14 showing the medial centers of the pedicle base circumferences.
Figure 16:
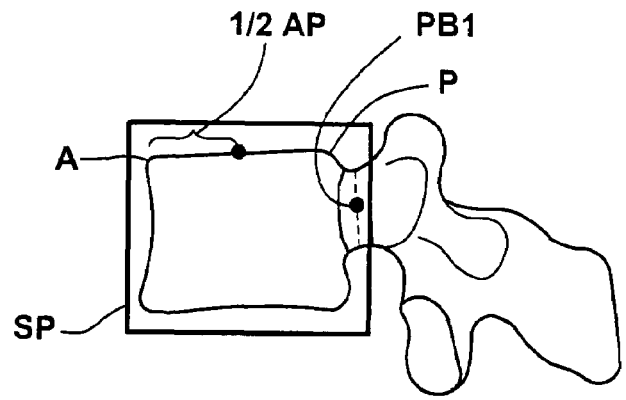
FIG. 16 is a sagittal view of a vertebra showing the medial center of the pedicle base circumference and the anterior and posterior points through the sagittal center of the endplate.
Figure 17:
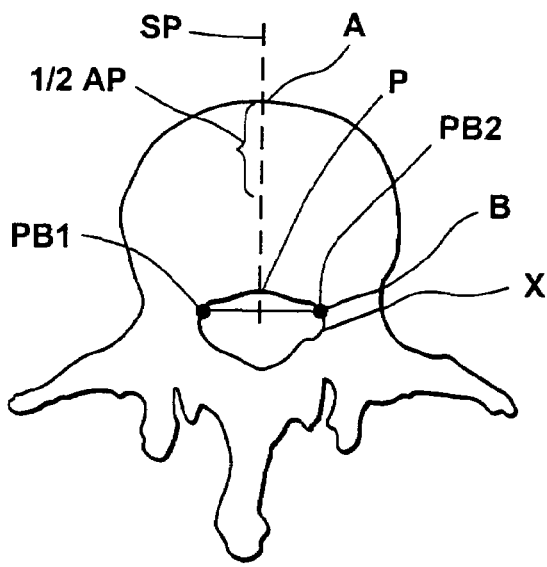
FIG. 17 is a schematic transverse view of the vertebra shown in FIG. 16.
Figure 18:
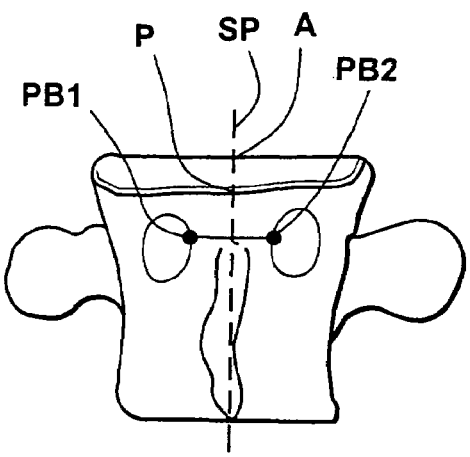
FIG. 18 is a schematic coronal view of the vertebra shown in FIGS. 16 and 17.

As shown in FIGS. 6-9, the computer then automatically determines the maximum allowable disc prosthesis to be placed by creating an artificial volume 2 corresponding to an actual prosthetic disc which is positioned according to a manufacturer's size and lordosis recommendations for its prosthesis. For example, one manufacturer's prosthesis may require a two millimeter anterior inset, whereas another manufacturer's prosthesis may require a three millimeter anterior inset. The manufacturers' recommendations vary from one prosthesis to another and apply to all four parameters of height, width, depth and lordosis. In addition, to assure the prosthetic disc is not oversized, the maximum artificial disc volume 2 is constrained such that its center of rotation 6 must lie posterior to the center 8 of the disc space 4, ideally in the posterior one-third, when the prosthesis is fully seated. As shown in FIGS. 10-12, this center of disc space 4 distance is defined by utilizing a pedicle base circumference method, described more fully hereinafter. The artificial prosthetic disc volume 2 will fit within the actual intervertebral disc space volume 4 except for specified height or lordosis alterations desired by the surgeon. Artificial discs are of two major designs, either as a single integrated unit or of multiple components.

Step 5

The pedicle base circumference outline method as shown in FIGS. 13-18 utilizes a computer generated image which demonstrates the pedicle base circumference B defined as the cortical junction between the pedicle walls and its transition into the vertebral body. Radiographically this is identified intraoperatively on both plain x-rays and fluoroscopic images as the circular-like cortical outline commonly seen in an anteroposterior direction at the superior lateral aspect of the vertebral body. By using the medial center of each pedicle base circumference B to its vertebral body as a reference point PB1 or PB2, a line can then be drawn to connect these two points PB1-PB2. From this line, a sagittal plane SP is made perpendicular to the PB1-PB2 line. The intersection of the sagittal plane SP with the respective vertebral endplates E defines the anterior point A and posterior point P which is the distance through the sagittal center of the endplate E. One-half of this distance from A-P (½ A-P) is the center of the vertebral endplate, point C. This center point C is depicted on the actual disc space volume for individual and merged volume image analysis.

Step 6

For those disc spaces in which the surgeon desires to restore lost disc height or lordosis secondary to disc degeneration, the computer can modify the artificial disc space volume to incorporate these desired changes and include them in the idealized schematic volume table.

Step 7

Figures 19, 20:
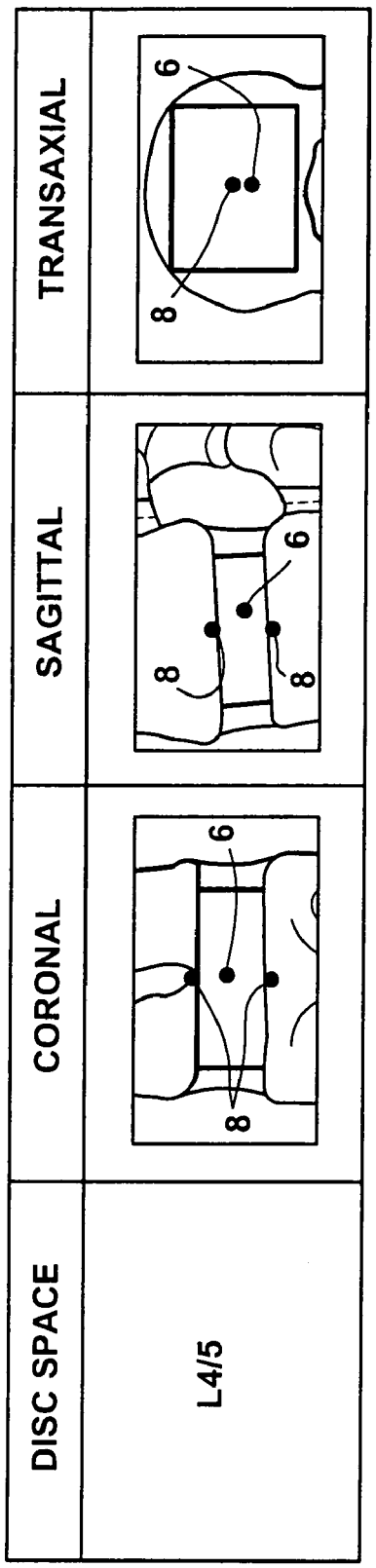
FIG. 19 is a portion of a schematic volume table that is generated to show the positioning of the prosthetic disc relative to the disc space between vertebrae in the coronal, sagittal and transaxial (or transverse)planes.
FIG. 20 is a table showing maximum size parameters for the intervertebral disc space that may be generated in accordance with the present invention.

The computer then provides a data summary table, (See e.g., FIGS. 19 and 20) which displays the ideal prosthetic disc height, width, depth and lordosis for each intervertebral disc space and also provides an idealized schematic drawing of the actual disc space volume and the prosthetic disc space volume individually and merged together. These volumes will include the center points for visualization. Individual vertebra are labeled by having the surgeon identify any specific vertebra and then the computer automatically labeling the remaining vertebral bodies and the surgeon confirming accurate vertebral labeling.

Step 8—Method A: Manual Artificial Disc Placement

The surgeon utilizes the idealized schematic diagram and summary data for prosthetic disc placement by a manual preferred method.

Step 9—Method B: Pedicle Base Circumference Outline Method

This method utilizes a computer generated image which demonstrates the pedicle circumference B defined as the cortical junction between the pedicle wall and its transition into the vertebral body. Radiographically this is identified intraoperatively on both plain x-rays and fluoroscopic images as the circular-like cortical outline commonly seen in an anteroposterior direction at the superior lateral aspect of the vertebral body.

This is a consistent radiographic landmark which can be utilized for artificial disc placement. The fluoroscopic or image guidance image is aligned to be parallel to the caudad superior endplate. Furthermore, the vertebral body is centered by having its center equidistant from each pedicle base circumference within the fluoroscopic AP image and with its superior endplate visualized usually by symmetric disc space with the cephalad vertebral body.

Figure 21:
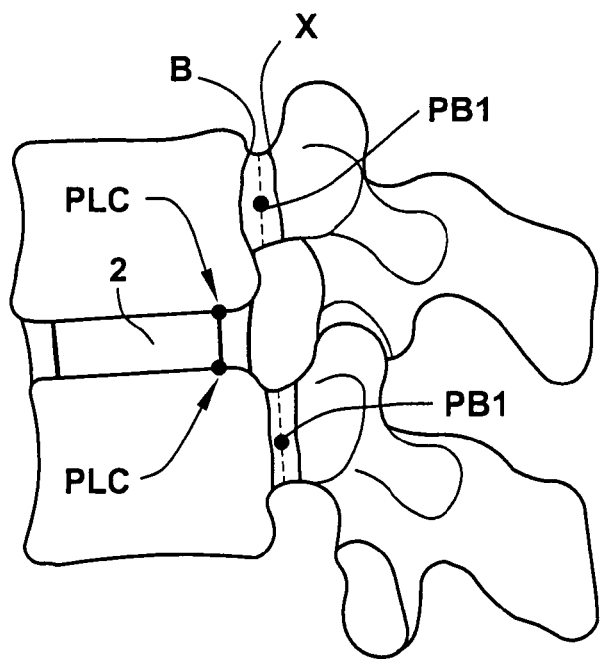
FIG. 21 is a schematic sagittal view in elevation of adjacent vertebrae showing the medial centers of the pedicle base circumferences and a prosthetic disc positioned in the space between the vertebrae.
Figure 22:
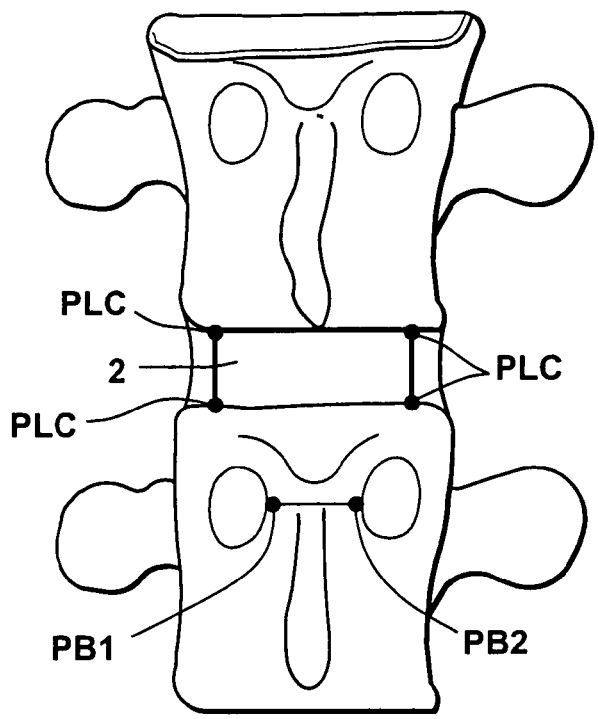
FIG. 22 is a schematic coronal view in elevation of the vertebrae shown in FIG. 21.
Figure 23:
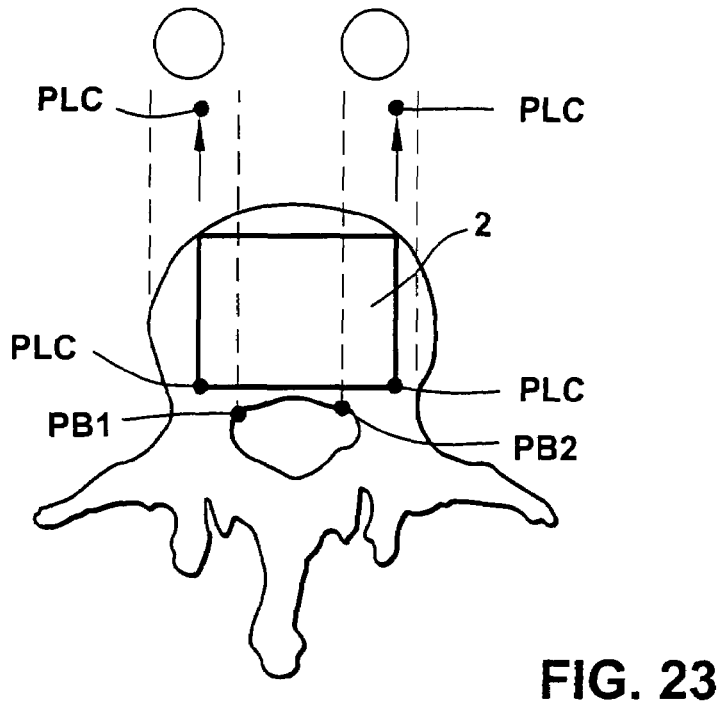
FIG. 23 is a schematic transverse view of the vertebrae shown in FIGS. 21 and 22 and includes pedicle base circumferences with posterolateral corners seen on a coronal view.

Insertion of the prosthetic disc can be undertaken in anterior, lateral or posterior approaches. The posterior most aspect of the prosthetic disc will lie in nearly the same plane as the pedicle base circumference line connecting the medical centers PB1-PB2 of the pedicle base circumferences. Thus, the superior and inferior posterolateral corners PLC of the prosthetic disc 2 can be labeled to identify this radiographically for positioning with respect to the pedicle base circumferences on the AP view and confirmed on the lateral view. This is shown in FIGS. 21-23.

Step 10—Method C: Dual Ring Apparatus and Drill Guide

Figure 24:
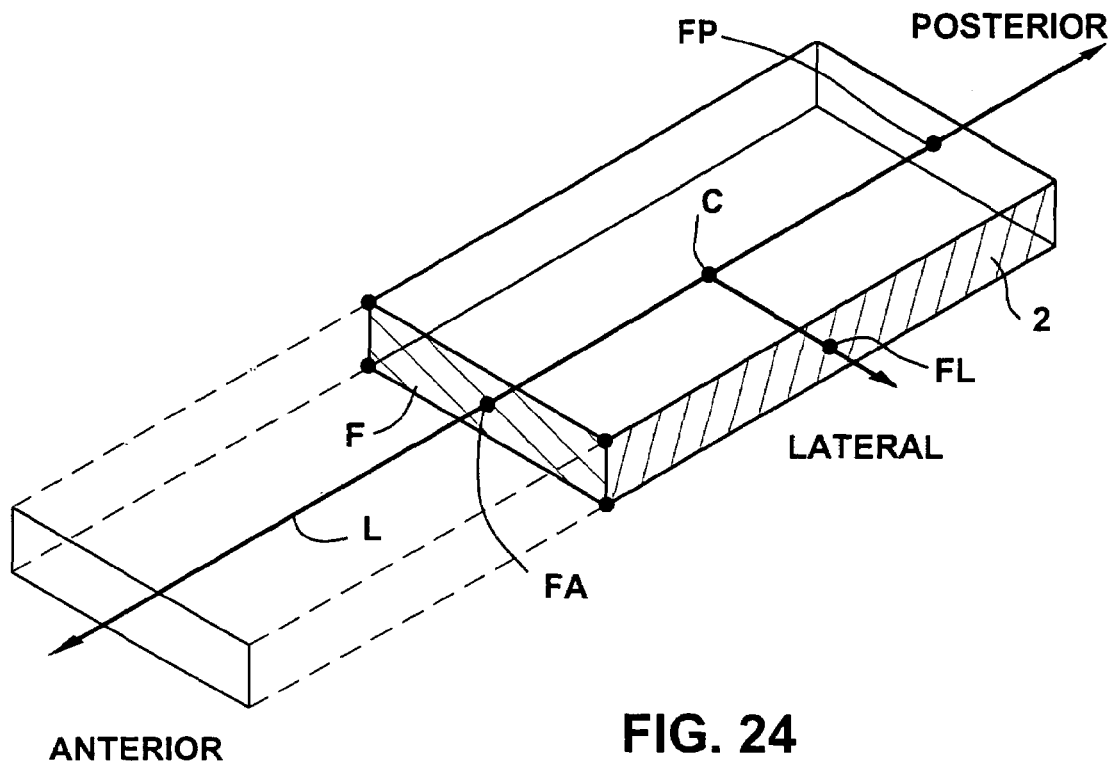
FIG. 24 is a schematic perspective view of a prosthetic disc volume in which center lines are present for the alignment and positioning of the prosthetic disc.

For automated intraoperative prosthetic disc placement, the dimensionally true three dimensional spine model with computer automated prosthetic disc space volumes can be utilized. In addition, a line L is drawn from the center point C of the prosthetic disc volume 2 to the center of the face, point F, of the disc from the approach it will be inserted to create a prosthetic disc volume which now has a line exiting out of the prosthetic disc volume at the anterior face FA, the posterior face FP or the lateral face FL, as shown in FIG. 24.

Step 11

Figure 25:
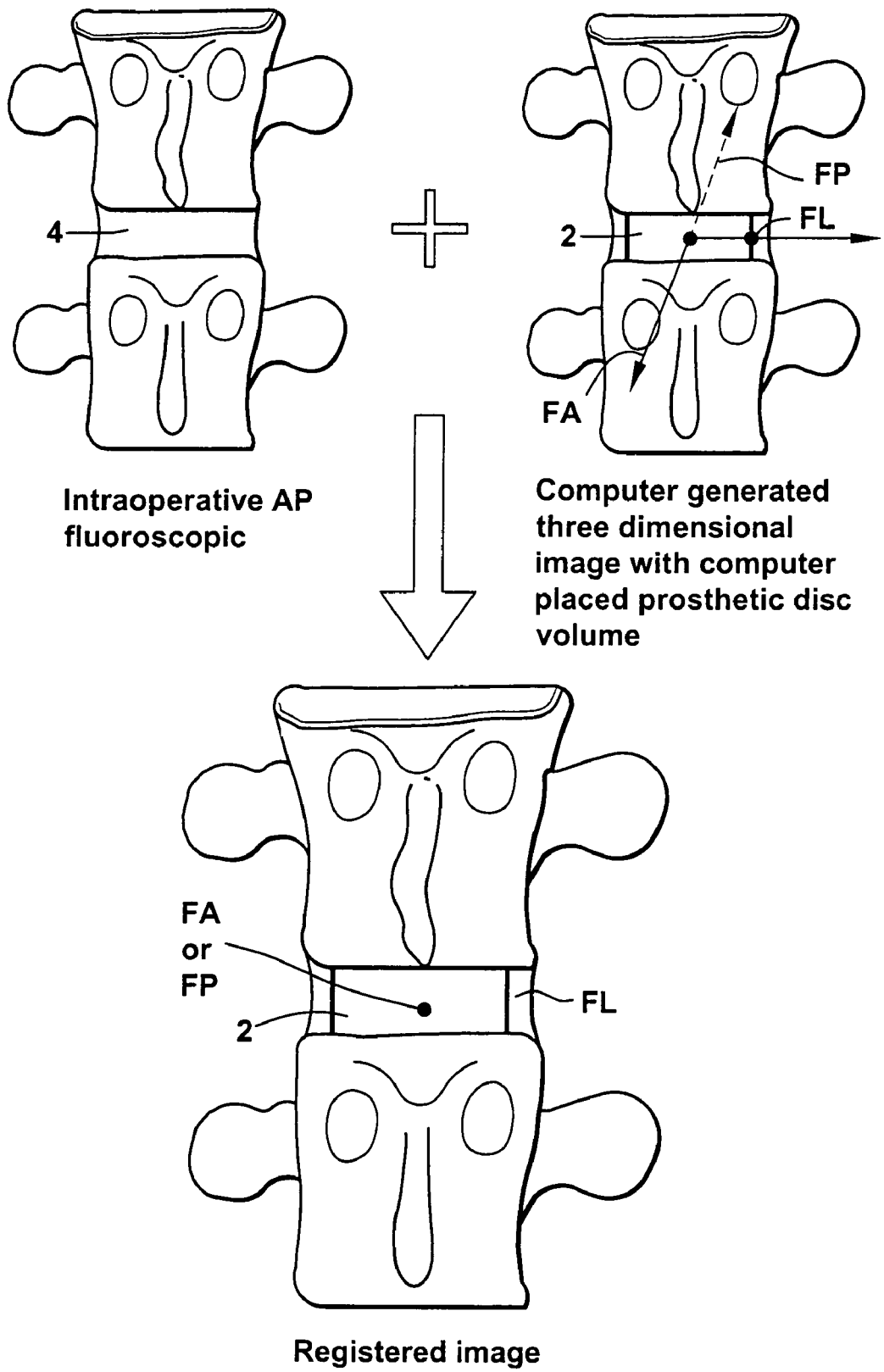
FIG. 25 is a schematic view showing adjacent vertebrae in the coronal plane and the steps of positioning a prosthetic disc therebetween in accordance with one of the methods of the present invention.

Referring to FIG. 25, real time intraoperative fluoroscopy is utilized for accurate registration with the there dimensional model on an individual vertebral basis. This fluoroscopic vertebral body image is centered on the monitor and identified by the surgeon for its specific vertebral body identifier (i.e., L4, L5 etc.). The corresponding dimensionally true three dimensional individual vertebral models are registered to this fluoroscopic image. This can be performed on either surgically exposed spines or percutaneously.

Step 12

The registration occurs by utilizing internal vertebral body landmarks. These landmarks are the pedicle base circumferences B seen on the fluoroscopic image which arise from the confluence of the pedicle cortical walls joining the vertebral body. These pedicle base circumferences B form either circular or elliptical shapes which can change configuration and square area based on vertebral body rotation with respect to fluoroscopic imaging.

Step 13

The intraoperative fluoroscopic and computer spine generated pedicle base circumference outlines are then registered. Precision of registration is obtained by assuring outlines are superimposed and measured square areas are equal; and by assuring distance between pedicles is equal. This method of registration eliminates the requirement of having a radiographic marker anchored to the patient's skeleton. This method also allows for free independent movement of one vertebral body to another demonstrating compliance of this computer generated model, which is particularly useful in spines with instability. The surgeon confirms adequacy of registration of pedicle circumferences intraoperatively in order to proceed with prosthetic disc placement. This method allows for magnification or reduction of the computer generated model to match the intraoperative fluoroscopic image.

Step 14

Figure 26:
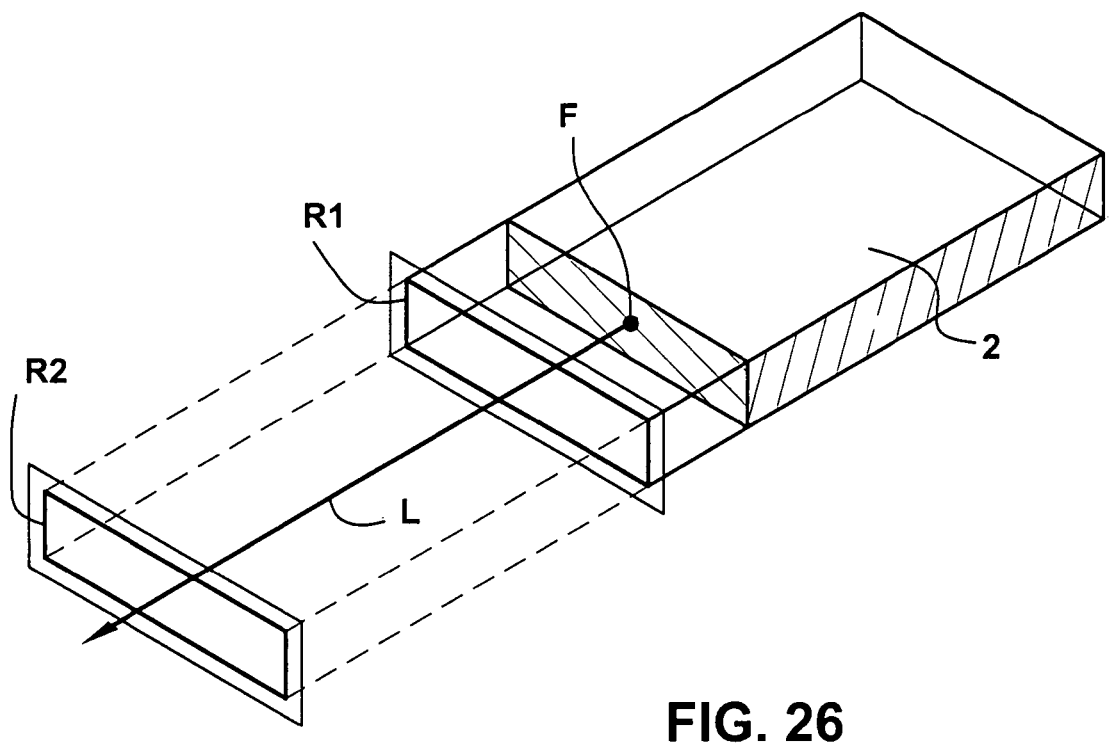
FIG. 26 is a perspective view similar to FIG. 24 showing a prosthetic disc volume for positioning in accordance with a two ring aligning apparatus.
Figure 27:
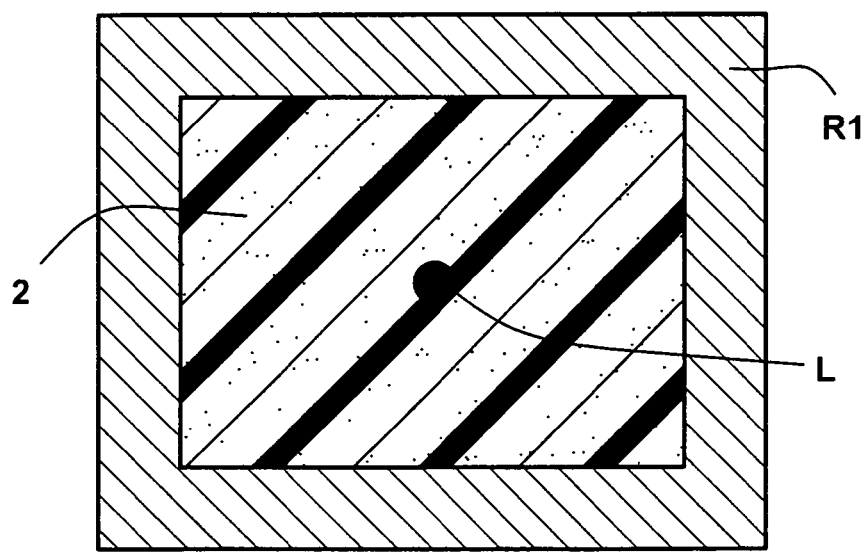
FIG. 27 is a schematic view generated by a computer of a prosthetic disc volume having a central line and a surrounding alignment ring.
Figure 28A:
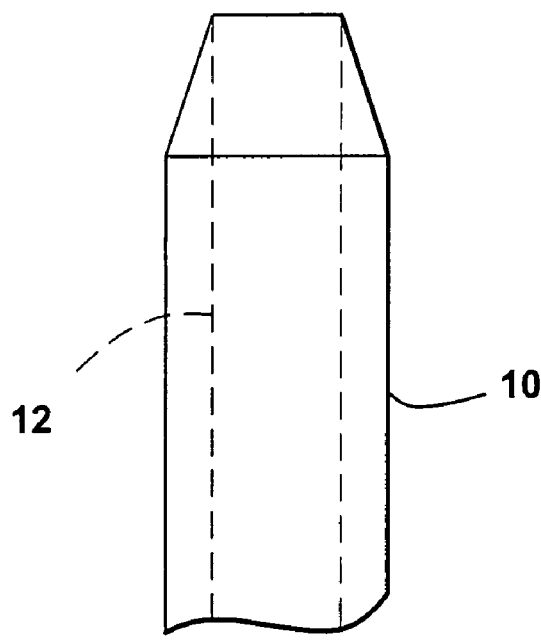
FIGS. 28a and 28b are side and front elevational views of the end portion of a first embodiment of a drilling cannula member for the dual ring aligning apparatus shown in FIG. 26.
Figure 28B:
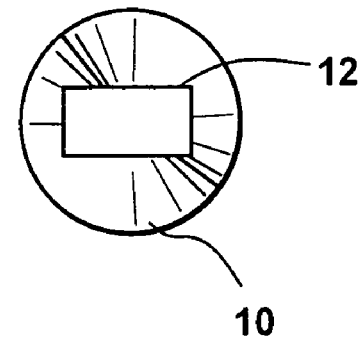
Figure 29A:
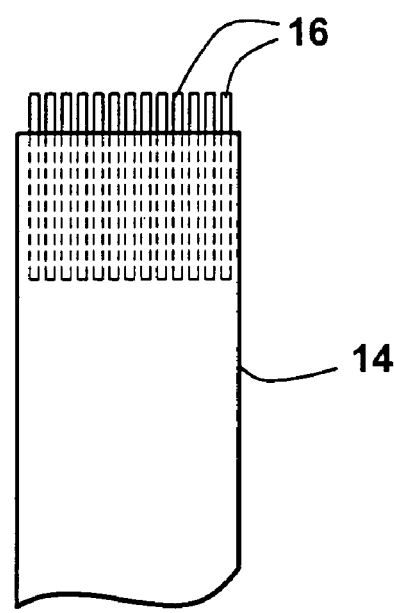
FIGS. 29a and 29b are side and front elevational views of the end portion of a second embodiment of a drilling cannula member for the dual ring aligning apparatus shown in FIG. 26.
Figure 29B:
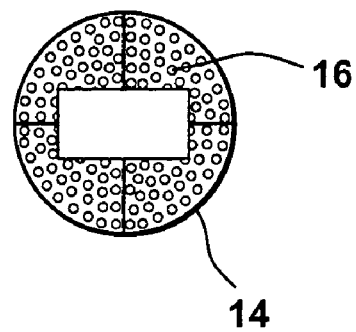

Referring to FIGS. 26 and 27, the three full dimensional image which now includes the computer generated pedicle base circumference and prosthetic disc volume 2 and central line L is then projected superimposed on the intraoperative fluoroscopic image. The computer prosthetic disc volume 2 is then projected out of the patient's body through the disc space and is intercepted by two separate and collinear rings R1 and R2. These rings are mounted on a device (not shown) anchored to the patient's bed and are oversized to allow interception of the computer volume image and to allow placement of drilling cannulas. The first ring R1 intercepts the computer prosthetic disc volume 2 near the disc space cortical region and the second ring R2 intercepts the computer prosthetic disc volume at any desired distance from the first ring R1. The longer the distance between the two rings, the greater the accuracy of prosthetic disc placement. The interception of the computer prosthetic volume by the rings is manually performed which is displayed real-time on the computer monitor which demonstrates movement of the rings with respect to the computer prosthetic volume.

Step 15

Interception of the prosthetic disc volume occurs on two levels. The computer prosthetic volumes are comprised of a central line L with surrounding volume. First, the rings R1 and R2 need to be centered to both the central line L and surrounding volume. Second, the rings are registered to the body so their movements can be followed on the computer monitor probably through LED, EMF or other devices. Third, the rings are designed to have inner sizes to allow matching of the sizes of the computer generated prosthetic disc volumes. A variety of fixed ring sizes are available to allow utilization of any artificial disc system desired by the surgeon or the rings can be designed to have apertures allowing for variable sizes to allow matching of sizes corresponding to the sizes of the computer generated prosthetic disc volumes. Registration of the rings with the computer prosthetic disc volume is identified and confirmed on the computer monitor.

Step 16

The two co-aligned rings R1 and R2 now form the conduit in which to place a cannula 10. This cannula is also secured rigidly to the device anchored to the patient's bed. Inside this drilling cannula is placed either a solid drilling cannula 12 or a specialized inner cannula 14 which has multiple narrow metal parallel pins 16 contained within the cannula and centrally is clear to allow for drill placement. The multiple pins 16 allow for the inner cannula to rest evenly on an uneven surface. This feature provides additional stability at curved cortical surface drilling areas to avoid toggling of the drill bit. Additionally, this specialized inner cannula allows for retraction of the multiple parallel pins to allow fluoroscopic visualization of drilling within the disc space. Either method may be chosen by the surgeon. For use of the variable aperture diameter ring method, a solid cannula which contains two separate variable apertures can be utilized.

Step 17

The disc space is drilled to the desired precalibrated depth and not exceeding the predetermined artificial disc depth.

Step 18

The disc space is sounded to assure osseous integrity.

Step 19

Figure 30:
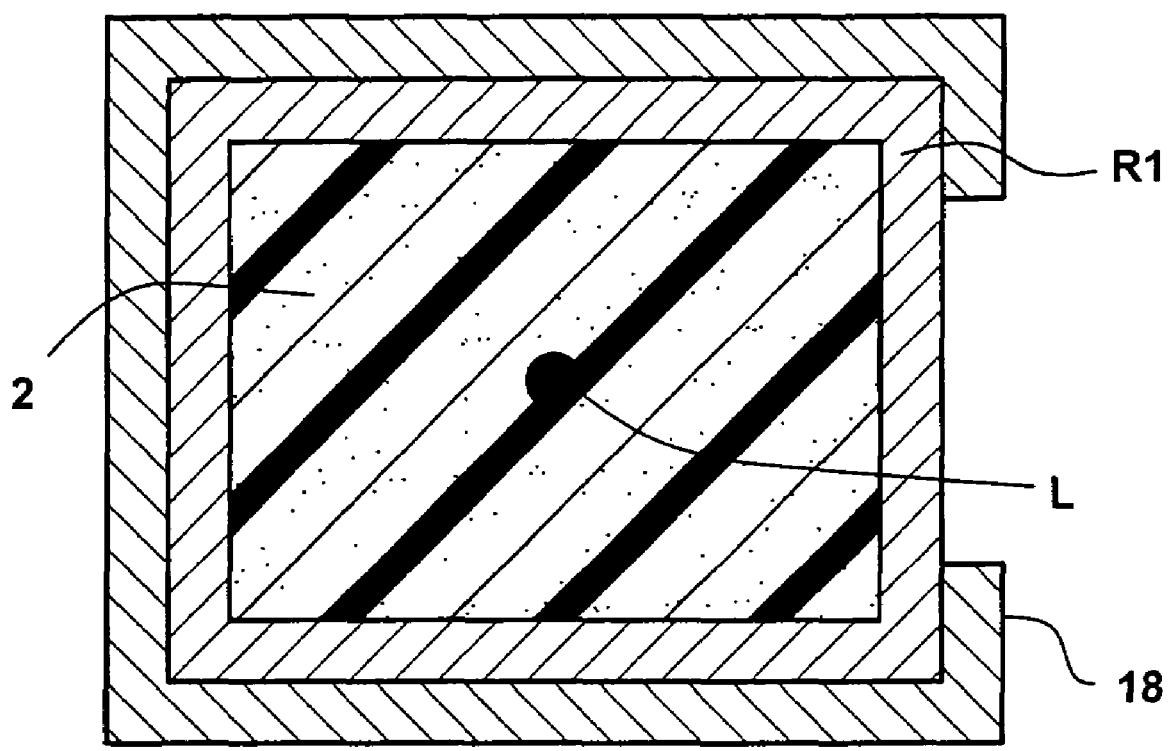
FIG. 30 is a schematic view similar to FIG. 27 showing a slotted outer cannula surrounding one of the ring members shown in FIG. 26.

For actual prosthetic disc placement a specialized slotted outer cannula 18 is placed collinear and onto the co-aligned two rings R1 and R2, as shown in FIG. 30. This specialized cannula 18 is also rigidly secured to the anchoring device. The rings R1 and R2 are then removed by withdrawing them from the cannula 18. The inner size of the cannula 18 is sufficient to accommodate any prosthetic disc size. The appropriate prosthetic disc is placed into its holding screwdriver (not shown), placed into the slotted cannula 18 and then placed into its respective disc space. For the variable aperture rings, the apertures are opened fully to allow placement of the screwdriver holding the appropriate prosthetic disc.

Step 20

The process is repeated for all desired disc spaces.

Step 21

There are currently commercially available software packages capable of producing intraoperative registration of intraoperative fluoroscopy images with preoperative three dimensional images of a patients' spine. Those capabilities an be integrated with the present invention to provide summary numerical data and idealized illustrated diagrams. The latter information will provide the basis for actual prosthetic disc placement as described in this invention or by a surgeon's preferred choice.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

What is claimed is:

1. A method of determining a size and/or placement of a prosthetic disc in a disc space between adjacent endplates of two vertebrae in a selected spinal area, comprising the computer implemented steps of:

identifying the disc space parameters of height, width, depth and lordosis between the adjacent vertebral endplates;

creating a prosthetic disc volume corresponding to an actual prosthetic disc that can be positioned in the disc space in accordance with a manufacturer's size and lordosis specifications for prosthesis;

determining a center of the disc space and a center of rotation of the prosthetic disc volume;

positioning the prosthetic disc volume in the disc space such that the center of rotation of the prosthetic disc volume is positioned posterior to the center of the disc space; and determining the prosthetic disc volume that fits within the disc space in accordance with a surgeon's or manufacturer's specification for prosthesis.

2. The method of claim 1 wherein the center of the disc space is determined by identifying the medial center points of the pedicle base circumferences of one of the vertebrae, creating a straight line between the medial center points, creating a sagittal plane perpendicular to said straight line such that the sagittal plane intersects with the vertebral endplates at an anterior point and a posterior point, and identifying the center of the disc space as one-half the distance between the anterior point and the posterior point along the sagittal plane.

3. The method of claim 1 wherein a computer is used to create tables showing the height, width, depth and lordosis of both the disc space and the prosthetic disc volume.

4. The method of claim 3 wherein a computer is used to create a schematic diagram identifying data for different intervertebral disc spaces.

5. The method of claim 1 further comprising identifying the medial center points of the pedicle base circumferences of one of the vertebrae, creating a straight line between the center points, identifying the corners of the prosthetic disc volume, and using a computer to register the corners of the prosthetic disc volume with the straight line to aid in the positioning of the prosthetic disc volume in the disc space.

6. The method of claim 1 further comprising using a dimensionally true three dimensional spine model with computer automated prosthetic disc volumes for automated intraoperative prosthetic disc placement.

7. The method of claim 6 wherein a computer generates a straight alignment line extending from the center of rotation of the prosthetic disc volume through the anterior, posterior or lateral faces of the prosthetic disc volume.

8. The method of claim 7 wherein real time intraoperative fluoroscopy is used for accurate registration of the prosthetic disc volumes, with the three dimensional spine model.

9. The method of claim 6 wherein the generated line and extended prosthetic disc volume are intercepted by and extend through a pair of spaced collinear rings that are mounted on a frame supported by a patient's bed or other support, one of said rings being located near the prosthetic disc volume and the other of said rings being spaced outwardly from the one ring, said rings having an inner size that is approximately the same as the size of the prosthetic disc volume extending therethrough, said rings providing a guide for a drilling cannula to form an opening corresponding to the generated prosthetic disc volume.

10. The method of claim 9 wherein said rings are movably mounted on said frame.

11. The method of claim 9 wherein said rings are removably mounted on said frame.

12. The method of claim 9 wherein each of said rings is adjustable to vary the inner size thereof.

13. The method of claim 9 wherein a drilling cannula is inserted through said rings and is provided with a central longitudinal opening for a movable support of a drilling member.

14. The method of claim 13 wherein said drilling cannula is mounted on a patient's bed or other support and comprises an inner cannula member for movable support of the drilling member.

15. The method of claim 14 wherein said inner cannula member comprises spaced, parallel, longitudinally extending and movable pins which define the central opening for the drilling member, said pins being extendable beyond the inner end of the drilling cannula to provide stable support thereof on uneven surfaces.

16. The method of claim 13 wherein said rings are movably mounted on said frame and, after the drilling of the opening and removal of the drilling cannula, a second cannula having a longitudinal slot therethrough is mounted on the exterior of said rings and is secured to said frame so that the longitudinal axis thereof corresponds to the longitudinal axis of the generated prosthetic disc volume extending through said rings, said second cannula serving as a guide for the insertion of a prosthetic disc into the disc space after said rings are removed from said second cannula.

17. A method of determining a size and/or placement of a prosthetic disc in a disc space between adjacent endplates of two vertebrae in a selected spinal area, comprising:

identifying the disc space parameters of height, width, depth and lordosis between the adjacent vertebral endplates;

creating an a prosthetic disc volume corresponding to an actual prosthetic disc that can be positioned in the disc space in accordance with a manufacturer's size and lordosis specifications for prosthesis;

determining a center of the disc space and a center of rotation of the prosthetic disc volume;

positioning the prosthetic disc volume in the disc space such that the center of rotation of the prosthetic disc volume is positioned posterior to the center of the disc space;

determining the prosthetic disc volume that fits within the disc space in accordance with a surgeon's or manufacturer's specification for prothesis; and placing the prosthetic disc in the disc space between the adjacent endplates of two vertebrae in the selected spinal area based upon the determination that the prosthetic disc volume fits within the disc space.

\* \* \* \* \*